(12) United States Patent
Chow et al.

(10) Patent No.: US 7,329,416 B2
(45) Date of Patent: Feb. 12, 2008

(54) METHOD OF ENHANCING ABSORPTIONS OF TRANSMUCOSAL ADMINISTRATION FORMULATIONS

(75) Inventors: Sing Sum Moses Chow, Glastonbury, CT (US); Yan-feng Wang, Hong Kong (CN); Zhong Joan Zuo, Hong Kong (CN)

(73) Assignee: The Chinese University of Hong Kong, Shatin, N.T., Hong Kong SAR (CN)

(*) Notice: Subject to any disclaimer, the term of this patent is extended or adjusted under 35 U.S.C. 154(b) by 0 days.

(21) Appl. No.: 11/220,491

(22) Filed: Sep. 7, 2005

(65) Prior Publication Data

US 2006/0051415 A1    Mar. 9, 2006

Related U.S. Application Data

(63) Continuation-in-part of application No. 10/935,899, filed on Sep. 8, 2004, now abandoned.

(51) Int. Cl.
*A61K 9/68*    (2006.01)

(52) U.S. Cl. ...................................... 424/440; 424/464

(58) Field of Classification Search ................ 424/440, 424/464
See application file for complete search history.

(56) References Cited

U.S. PATENT DOCUMENTS 5,855,908 A * 1/1999 Stanley et al. ............... 424/440
6,255,502 B1 * 7/2001 Penkler et al. ............... 552/549

OTHER PUBLICATIONS

Data sheet containing product information on APO-PROPRANOL prepared on Jun. 24, 1999.
Data sheet containing product information on ANGILOL prepared Jan. 28, 1999.

* cited by examiner

*Primary Examiner*—Yvonne Eyler
*Assistant Examiner*—Sudhakar Katakam
(74) *Attorney, Agent, or Firm*—Knobbe, Martens, Olson & Bear LLP (57) ABSTRACT

Disclosed is a method for enhancing absorption of a medicament that is suitable for administering transmucosally to a subject by providing an environment of the administration with a suitable pH. A medicament of propranolol suitably administered sublingually is provided. The medicament of propranolol can be used for treating diseases related to the cardiovascular system.

14 Claims, 4 Drawing Sheets

METHOD OF ENHANCING ABSORPTIONS OF TRANSMUCOSAL ADMINISTRATION FORMULATIONS

CROSS-REFERENCE TO RELATED APPLICATIONS

This is a continuation-in-part of prior U.S. application Ser. No. 10/935,899, filed on Sep. 8, 2004 now abandoned which is hereby incorporated herein by reference in its entirety.

BACKGROUND OF THE INVENTION

1. Field of the Invention

The present invention is directed to a method for enhancing absorption of a medicament that is suitable for transmucosal administration, particularly to a method for enhancing absorption of a medicament suitable for sublingual administration.

2. Description of the Related Art

Transmucosal drug delivery system has been studied for years because it can avoid the liver first-pass effect. The study on this field focuses on how to enhance absorption of the drug. General approaches reported to enhance absorption include the use of various permeation enhancers such as bile salts, surfactants, organic solvents, chelating agents as well as salicylate and Azone®.

Factors affecting the permeation of a drug via oral mucosa, such as sublingual mucosa, include solubility of the drug, partition coefficient, degree of ionization of the drug, and molecular size and weight of the drug. For a given drug, the molecular size and weight are fixed and cannot be changed. Changes in solubility and degree of ionization will influence partition coefficient and permeability. Therefore, optimization of combined solubility and ionization are variable factors to achieving maximum rate and extent of absorption through oral mucosa such as sublingual mucosa.

SUMMARY OF THE INVENTION

A first aspect of the preferred embodiments provides a method for enhancing absorption of a medicament that is suitable for administering transmucosally, such as sublingually in a subject. The medicament used in the preferred embodiments includes a therapeutically effective amount of an active compound or a pharmaceutically acceptable form thereof, or a combination thereof and a pharmaceutically acceptable carrier.

The inventors have found that maximum flux of ionized and non-ionized forms of an active compound of a medicament across the mucosal membrane can be achieved with the attainment of a pH in a mucosal medium by involving certain amount of buffering agents with the medicament. The method of the preferred embodiments comprises providing an environment for the administration with a pH of about:

$$pH = -\log\left(\frac{Ka \cdot S_i}{S_u}\right) \quad (I)$$

in which $K_a$ is the ionization constant (dissociation constant) of the active compound in water, $S_i$ is the solubility of the ionized form of the compound, and $S_u$ is the solubility of the non-ionized form of the compound.

A second aspect of the preferred embodiments is to provide a method for enhancing absorption of a medicament comprising propranolol or a pharmaceutically acceptable form thereof that is administered transmucosally to a subject, comprising providing an environment of the administration with a pH range of about 7.2 to about 7.8.

A third aspect of the preferred embodiments is to provide a medicament suitable for a transmucosal administration to a subject, comprising an effective amount of propranolol or a pharmaceutically acceptable form thereof, and a pharmaceutically acceptable carrier, in which the medicament provides an environment of the administration with a pH range of about 7.2 to about 7.8.

A fourth aspect of the preferred embodiments is to provide a method for treating cardiovascular diseases of a subject comprising transmucosally administering a therapeutically effective amount of propranolol or a pharmaceutically acceptable form thereof to the subject in an environment with a pH range of about 7.2 to about 7.8.

Compared to a conventional formulation of propranolol, the formulation of the preferred embodiments can significantly decrease the heart rate in a subject in a very short time, and can be used to treat cardiovascular related diseases (urgent medical conditions) such as atrial fibrillation with rapid heart rate, panic attacks with rapid heart rate, acute hypertension, headache and angina.

DETAILED DESCRIPTION OF THE PREFERRED EMBODIMENT

As stated above, the preferred embodiments provide a method for enhancing absorption of a medicament that is suitably administrated transmucosally. In one embodiment, the medicament is administered sublingually by adjusting the pH of the environment of administration of the medicament. We found that an active compound of a medicament can be significantly absorbed when an environment of the administration of the medicament is kept around:

$$pH_{max} = -\log\left(\frac{Ka \cdot S_i}{S_u}\right) \quad (I)$$

in which $K_a$ is the ionization constant (dissociation constant) of the active compound of the medicament in water, $S_i$ is the solubility of the ionized form of the compound, and $S_u$ is the solubility of the non-ionized form of the compound. $S_i$ and $S_u$ can be easily obtained by measuring the drug solubility at two extreme pH levels where the ionized or non-ionized species are dominating. For example, after determining the $S_i$ and $S_u$ of propranolol and sildenafil, their $pH_{max}$ values are calculated to be 7.62 and 4.25, respectively.

Theoretically, an ionizable medicament to transport across the mucosa includes both the ionized form and the non-ionized form of the medicament. The overall steady-state flux ($J_{ss}$) and the apparent permeability coefficient ($P_{app}$) of a medicament across the mucosa are the summations of the individual contribution from both the ionized and the non-ionized forms. Therefore, the $J_{ss}$ and $P_{app}$ of such a medicament permeate across the mucosa can be expressed by the following equations:

$$J_{ss(u)} = \frac{dQ_u}{dt \cdot A} = P_u C_u \quad (1)$$

$$J_{ss(i)} = \frac{dQ_i}{dt \cdot A} = P_i C_i \quad (2)$$

$$J_{ss} = J_{ss(u)} + J_{ss(i)} \quad (3)$$

$$P_{app} = P_i X_i + P_u X_u \quad (4)$$

$$C_0 = C_i + C_u \quad (5)$$

In the above equations, $J_{ss(u)}$ and $J_{ss(i)}$ are the steady-state flux of the ionized form and the non-ionized form of the medicament, respectively; $Q_u$ and $Q_i$ are the accumulated amount of the ionized form and the non-ionized form of the medicament penetrated across the mucosa, respectively; A is the surface area of the mucosa; $C_0$ is the loading concentration of the medicament; $P_i$ and $P_u$ are the permeability coefficient of the ionized form and the non-ionized form, respectively; $X_i$ and $X_u$ are the fraction of the ionized form and the non-ionized form, respectively; and $C_i$ and $C_u$ are the concentration of the ionized and non-ionized forms, respectively. Unlike $J_{ss(u)}$ and $J_{ss(i)}$, $P_i$ and $P_u$ are all independent of pH of the solution (environment). Therefore, we would expect that maximal $C_i$ and $C_u$ will be reached at an optimal $pH_{max}$, which will be the solubility of the ionized form ($S_i$) and the non-ionized form ($S_u$), respectively, and the maximal steady-state flux can be obtained accordingly.

$$(J_{ss})_{max} = P_i S_i + P_u S_u \quad (6)$$

$$\text{When } pH \leq pH_{max}, J_{ss} = P_i S_i + P_u S_i \frac{K_a}{[H^+]} \quad (7)$$

$$\text{When } pH > pH_{max}, J_{ss} = P_u S_u + P_i S_u \frac{[H^+]}{K_a} \quad (8)$$

It is expected that the best flux of the medicament across the mucosa would be achieved if we could achieve the $pH_{max}$ in the environment with a certain amount of buffering agents in a specific formulation of the medicament.

As used herein, the term "absorption", unless specified otherwise, means "penetration" of the active compound of the medicament through the mucosa.

The term "transmucosal", unless specified otherwise, means any route of the administration via the mucosal membrane. Examples include, but are not limited to, sublingual, nasal, vaginal and rectal. In the preferred embodiments, the administration is preferably performed sublingually.

The term "environment" or "environment of an administration" means an environment where an active compound of a medicament is absorbed by permeation across the mucosa. For example, when the administration is performed sublingually, the environment is saliva, which contains the drug and is "bathing" the sublingual mucosal membrane.

The term "subject" means animals and human. Human is preferable in the preferred embodiments.

The method of the preferred embodiments which provides an environment with a certain pH includes providing the environment with a preferable pH during the administration of the medicament, and making a suitable formulation of the medicament in such a way that the medicament itself can provide the environment with a desired pH. In the preferred embodiments, the latter is preferably. In this case, buffering agents are preferably involved in the formulation.

Buffering agents that can be used in the preferred embodiments will be obvious for those skilled in the art. Please see "Handbooks Pharmaceutical Excipients (Second Edition), edited by Ainley Wade and Paul J W Weller, The Pharmaceutical Press London, 1994", which is incorporated herein by reference. Exemplified buffering agents include, but are not limited to, phosphates, such as sodium phosphate; phosphates monobasic, such as sodium dihydrogen phosphate and potassium dihydrogen phosphate; phosphates dibasic, such as disodium hydrogen phosphate and dipotassium hydrogen phosphate; citrates, such as sodium citrate (anhydrous or dehydrate); bicarbonates, such as sodium bicarbonate and potassium bicarbonate. The amount of buffering agents used in the medicament is readily determined by those skilled in the art, which depend on preferable pH values.

The medicaments of the preferred embodiments can include various formulations dependent on the dosage forms or formulations of administration. For example, if the medicament is administered sublingually, it can be in the form of tablets, pills, pellets, powders or sprays. Examples of other suitable formulations include, but are not limited to, ointments, capsules, solutions, syrups, drops, granules and suppositories. In any formulation, the medicament can include a therapeutically effective amount of an active compound or a pharmaceutically acceptable form thereof or either entity and a pharmaceutically acceptable carrier. Examples of the active compounds include, but are not limited to, propranolol, scopolamine, estradiol, sildenafil, fentanyl, morphine, buprenorphine, butorphanol, methadone, diamorphine, piroxicam, flurbiprofen, indomethacin, naproxen, sulindac, tenoxicam and nifedipine. In the preferred embodiments, propranolol is preferable.

The carrier suitably used in the preferred embodiments depends on the specific formulation of the medicament, which is known by those skilled in the art. The carriers include, without limitation, fillers, binders, lubricants, diluents, sweetening and flavoring agents, preservatives, disintegrators, grilling agents, permeation enhancers. Examples of the carriers include starch, gelatin, natural sugars, corn, natural and synthetic gums such as acacia, sodium alginate, methylcellulose, carboxymethylcellulose, polyethylene glycol, waxes, boric acid, sodium benzoate, sodium acetate, sodium chloride, agar, bentonite, agar gum, stearates such as sodium stearate, HPMC, and palmitic acid, dimethyl sulfoxide, N,N-dimethyl acetamide, N,N-dimethylformamide, 2-pyrrolidone, 1-methyl-2-pyrrolidone, 1,5-dimethyl-2-pyrrolidone, 1-ethyl-2-pyrrolidone, 2-pyrrolidone-5-carboxylic acid, N,N-dimethyl-m-toluamide, urea, ethyl acetate, 1-dodecylazacycloheptan-2-one (Azone®), oleic acid, ethylene vinylacetate copolymer, polyvincyl chloride, polyethylene, polydiethyl phthalate.

Medicaments suitably used in the preferred embodiments are those suitably administered transmucosally which are well known by one skilled in the art.

Propranolol, 1-(isopropylamino)-3-(1-naphthyloxy)-2-propanol, a nonselective $\beta_1$ and $\beta_2$-adrenergic antagonist, has been widely used in the treatment, amelioration, or prophylaxis of diseases associated with cardiovascular system, such as essential arterial hypertension, ischemic heart disease and atrial fibrillation. The indication of the propranolol, for example, includes management of angina pectoris; long term prophylaxis after recovery from myocardial infarction; control of most forms of cardiac dysrhythmias; control of essential and renal hypertension; prophylaxis of migraine; control of anxiety and anxiety tachycardia; management of essential tremor; adjunctive management of thyrotoxicosis and thyrotoxic crisis; management of hypertrophic obstructive cardiomyopathy; management of phaeochromocytoma (with an alpha-adrenoreceptor blocking medicine), etc. At present, injection and oral tablets are the only two dosage forms marketed commercially. Intravenous or intramuscular administration of propranolol can achieve fast onset of action. However, they are inconvenient and not suitable for self-medication.

Though oral administration of propranolol tablets has proven to be safe and effective in the treatment of atrial fibrillation, its onset of action is usually over 1 hr. Also, due to extensive hepatic first-pass effect, it has a short plasma half-life (2.8-4.4 hr), and a low bioavailability (10-30%).

To overcome these drawbacks, the preferred embodiments provide a method for enhancing the absorption of a medicament comprising propranolol or a pharmaceutically acceptable form thereof that is administered transmucosally in a subject, comprising providing an environment for the administration with a pH range of about 7.2 to about 7.8; and a medicament of propranolol that is suitably administered sublingually to a subject. The medicament propranolol of the preferred embodiments comprises an effective amount of propranolol or a pharmaceutically acceptable form thereof, and a pharmaceutically acceptable carrier, provided that the medicament provides an environment of the administration with a pH range of about 7.2 to about 7.8.

In the preferred embodiments, the medicament contains an effective amount of propranolol or a pharmaceutically acceptable form thereof, and a pharmaceutically acceptable carrier as described above, which can be formulated as a tablet, pill, pellet, spray, or powder, preferably as a tablet for sublingual administration. In the formulation, active compound propranolol can be used in the form of any pharmaceutically acceptable form such as free base, acidic salts, hydrates thereof, and acidic salts of the hydrates. In the preferred embodiments, the acidic salt form of propranolol is preferable because propranolol is a weak base. The acidic salts include, but are not limited to, a salt with inorganic acids such as hydrochloride, sulfate, and phosphate; and a salt with organic acids such as maleate, benzsulfonate acid, and citrate. It should be understood that the dose forms suitable for sublingual administration will have the same indications as those for the conventional dose forms, such as disclosed on www.medsafe.govt.nz/profs.htm for Apo-Propranoal™ and Angilol™, which is hereby incorporated herein by reference in its entirety.

It has been investigated that permeability across the sublingual mucosa is dependent on the concentration of non-ionized propranolol in the environment. When a formulation of propranolol provides saliva with pH of about 7.2 to about 7.8, propranolol should maintain relatively high solubility as well as high fraction of non-ionized form in the saliva of human oral cavity. Preferably, the formulation for sublingual delivery is at about pH 7.6. This can be confirmed by equation (I). For propranolol: $S_i$ is 22.118 (mg/ml), $S_u$ is 0.539 (mg/ml) and $K_a$ is $10^{-9.23}$.

$$pH = -\log\left(\frac{10^{-9.23} \times 22.118}{0.539}\right) = 7.62$$

To achieve this, buffering agents chosen include sodium bicarbonate, sodium phosphate, or a combination of borates and sodium hydroxide. Preferable examples include buffering agents $Na_2HPO_4$, $Na_2HPO_4$—$NaH_2PO_4$, $Na_2HPO_4$-citric acid, and Tris-HCl. Specifically, disodium hydrogen phosphate, by weight of about 10-25%, was found to effectively control the pH of saliva to be about 7.2 to about 7.8.

The medicament of propranolol of the preferred embodiments comprises an effective amount of an active component, and a suitable carrier. The term of "effective amount" means about 0.01 to about 99.99% in the formulation by weight. Preferably, the active compound propranolol accounts for about 1-90% in the formulation by weight. More preferably, the active component accounts for about 2-50% in the formulation by weight, and most preferably, about 5-10% in the formulation by weight.

The amount of the active component mentioned in the preferred embodiments, unless specified otherwise, means the amount of free compound of propranolol. The formulation of the preferred embodiments can be prepared to contain an amount of propranolol as those commercially available such as about 10 mg, 20 mg, 40 mg, or 80 mg in a tablet. It is also suitable that the formation may contain propranolol in an amount less than that commercially available, when it is used for urgent situations. Those skilled in the art will readily determine a suitable amount of propranolol in a specific formulation suitable for a given patient.

EXAMPLE 1

| Ingredients | Weight (g) |
| --- | --- |
| Propranolol hydrochloride | 40 |
| Disodium hydrogen phosphate | 40 |
| Lactose monohydrate | 109 |
| HPMC | 20 |
| Magnesium stearate | 2 |

Propranolol powder was mixed with magnesium stearate. To the resulting mixture was added other components, and then commingled in a V-blender for 15 minutes. The thoroughly blended composition was compressed into 1,000 plain tablets, each with 5 mm in diameter and 2-3 mm in thickness.

EXAMPLE 2

| Ingredients | Weight (g) |
| --- | --- |
| Propranolol hydrochloride | 20 |
| Sodium dihydrogen phosphate | 40 |
| Lactose | 129 |
| HPMC | 20 |
| Magnesium stearate | 2 |

All ingredients were formed as 1,000 tablets in the same way as in Example 1.

EXAMPLE 3

| Ingredients | Weight (g) |
| --- | --- |
| Propranolol hydrochloride | 20 |
| Sodium dihydrogen phosphate | 1.5 |
| Disodium hydrogen phosphate | 38.5 |
| Lactose monohydrate | 109 |
| HPMC | 20 |
| Magnesium stearate | 2 |

All ingredients were formed as 1,000 tablets in the same way as in Example 1.

Experiment 1

Pharmacodynamic Investigations

I. Methods and Materials

Two healthy male subjects took part in the preliminary pharmacodynamic investigation of sublingual administration of buffered propranolol powder with 4 different buffering capacities as shown in Table 1.

TABLE 1

| Formulations | Dosage Forms | Propranolol (mg) | Buffering Agent | Saliva pH (Mean) | Disappeared (% Mean) |
| --- | --- | --- | --- | --- | --- |
| 1 | Powder | 20 | 0 | 7.13 | 45.64 |
| 2 | Powder | 20 | 38.2 mg $Na_2HPO_4$ and 1.8 mg $NaH_2PO_4$ | 7.37 | 48.34 |
| 3 | Powder | 20 | 40 mg $Na_2HPO_4$ | 7.64 | 55.56 |
| 4 | Powder | 20 | 20 mg $NaHCO_3$ | 7.88 | 44.35 |

The subjects had not taken any sublingual medicine 2 weeks prior to and during the period of the study. Alcohol and smoking were not permitted for 24 hr prior to, and for the duration of the study. Caffeine-containing products were also not allowed from 8 hr prior to, and during, each study period.

The subjects were placed in a seated position for about 30 min prior to baseline measurements being made. A Dinamap BP monitor (Wipro GE Co., USA) was used to record systolic, diastolic, and mean blood pressure and heart rate every minute for 10 minutes before administration of sublingual propranolol tablet. After sublingual administration, each subject was refrained from swallowing any propranolol or saliva until about 25 minutes, then the saliva was spit out and collected for pH measurement. Subsequently the mouth was rinsed 4 times with pure water. Pharmacodynamic parameters such as heart rate and blood pressure were measured. The heart rate change is shown in FIG. 1 The blood pressure changes were variable and no significant hypotension occurred.

II. Results

Figure 1:
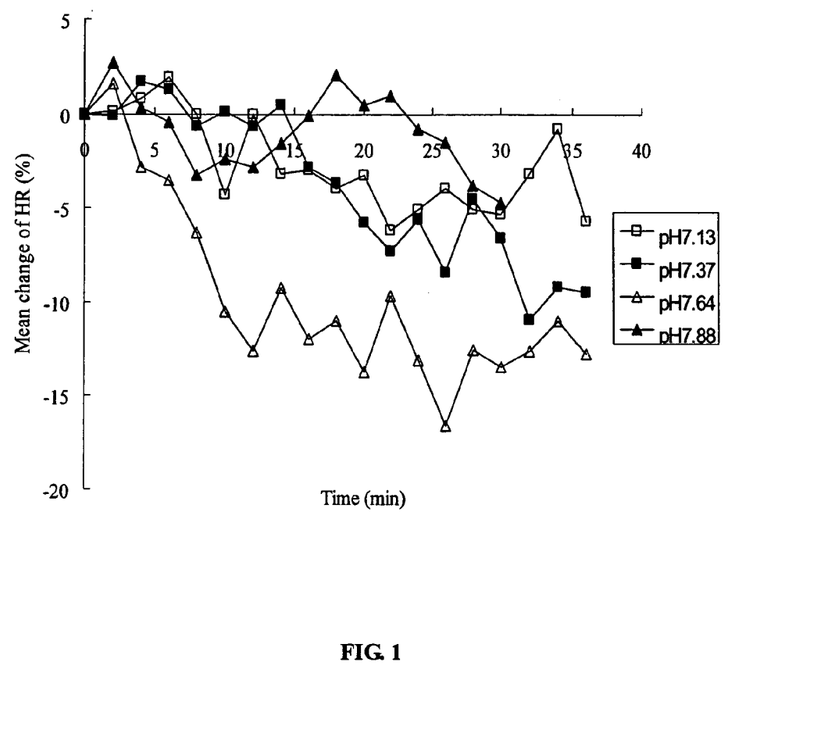
FIG. 1 shows mean heart rates of two healthy subjects after sublingually administering propranolol powder in various pH values.

The reduction of heart rate was highly dependent on the pH of saliva achieved from various buffering agents in the formulations (FIG. 1). Subjects receiving formulation 3 showed a drop of more than 10% of heart rate following 10 minutes of administration of sublingual propranolol, which is much faster onset of action than other formulations with different saliva pHs.

Moreover, the maximal reduction of heart rate was 17% for formulation 3, whereas only 5-10% maximal reductions were found for the other formulations. These results indicated that formulation 3 could effectively enhance the sublingual absorption of propranolol and rapidly reduce the heart rate in comparison to other 3 formulations.

Experiment 2

Control Test

I. Materials

Propranolol hydrochloride was ordered from Chang Zhou Guangming Biochemical Laboratories (BP 2000/USP24). Sodium dihydrogen phosphate and HPMC (50 cps) were supplied by Sigma-Aldrich Co. (St. Louis, Mo., USA). Lactose monohydrate was supplied by Fisher Scientific UK Ltd. (Leicestershire, UK). Magnesium stearate was obtained form Wing Hing (Hong Kong).

Inderal 40 mg propranolol tablets were purchased from AstraZeneca UK Ltd. (Macclesfield Cheshire, UK).

II. Methods

Two healthy male subjects took part in the preliminary pharmacodynamic investigation once with buffered sublingual propranolol tablets as prepared in Example 1 and the Inderal tablet in the same dose of 40 mg propranolol, respectively. The procedure of this study was similar to that described in Experiment 1 except that following the tablet, and the saliva was spit out in 8 minutes.

III. Results

Figure 2:
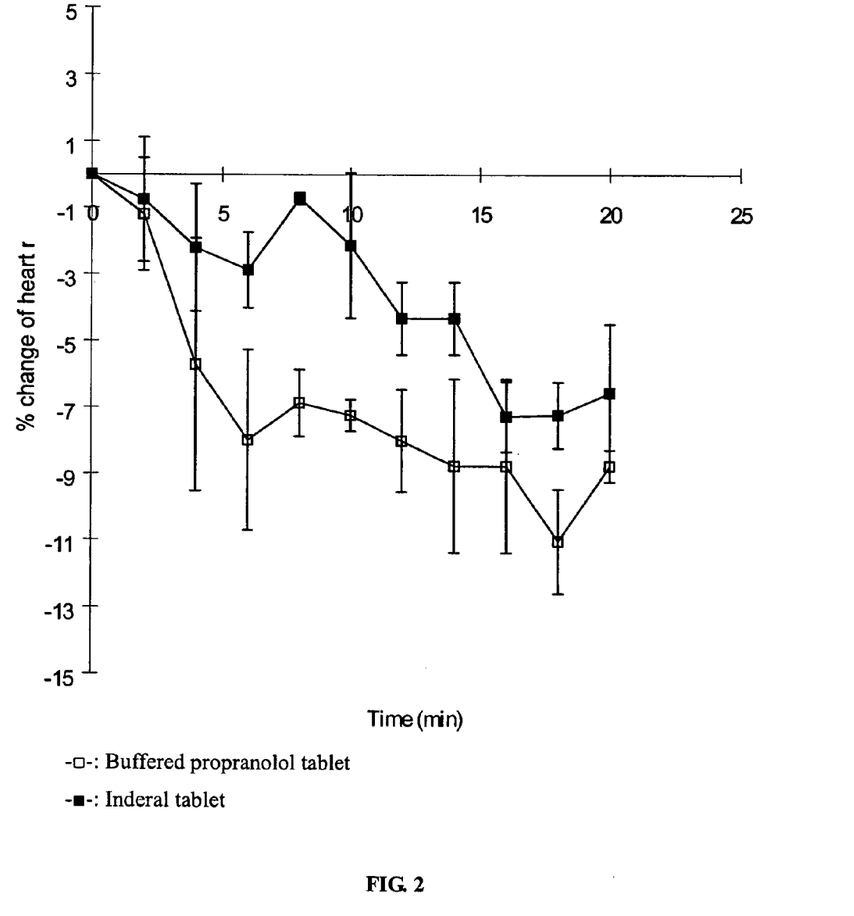
FIG. 2 shows a change of heart rate after administered with equivalent sublingual dose of a buffered propranolol tablet of the preferred embodiments versus a conventional Inderal tablet in 2 healthy subjects.

The saliva pH of the Inderal tablet and that of the buffered tablet of the preferred embodiments were shown in Table 2. These results were shown in FIG. 2. The results showed that the buffered formulation quickly reduced 8% heart rate after 10 min of sublingual administration. However, the effect of the Inderal tablet was delayed to over 15 minutes and only a 6% reduction of heart rate. The heart rate continued to decrease with both the formulations, reaching a maximum effect around 20 minutes. The mean maximum effect of the buffered propranolol tablet was about 12% reduction whereas the Inderal tablet only about 7% reduction. The effect on the blood pressure was variable following both the formulations and no significant hypotension was observed.

TABLE 2

| Dosage forms | Saliva pH (Mean ± SD) (n = 2) |
|---|---|
| Inderal tablet | 6.82 ± 0.10 |
| Buffered tablet | 7.52 ± 0.05 |

Experiment 3

Figure 3:
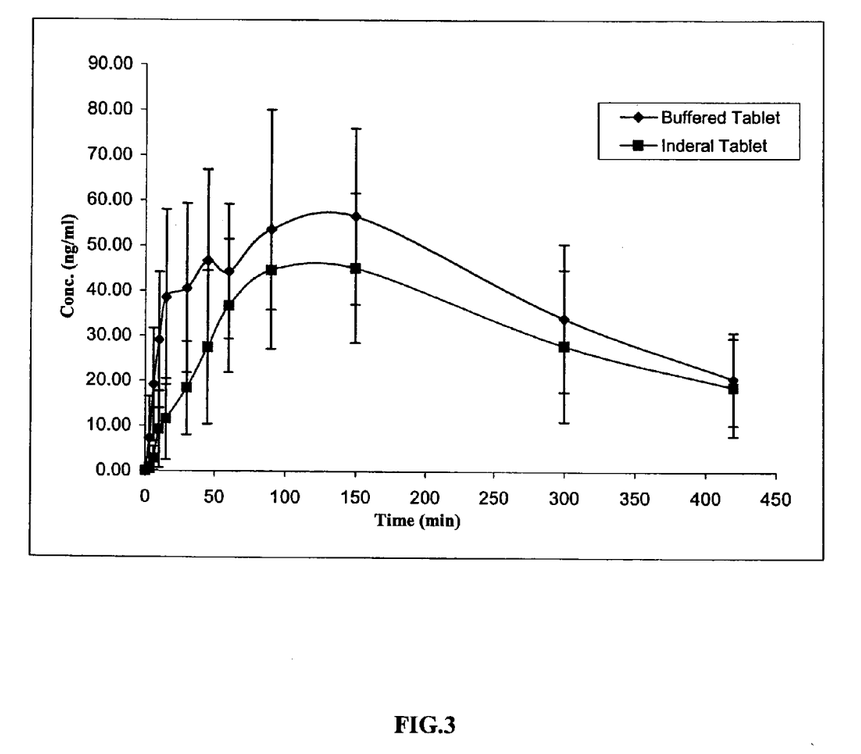
FIG. 3 shows time-plasma concentration profiles (0-420 min) of buffered propranolol tablets of the invention and Inderal (conventional tablet) in 8 male healthy subjects (*$p<0.05$, **$p<0.01$ by paired-samples t-test).
Figure 4:
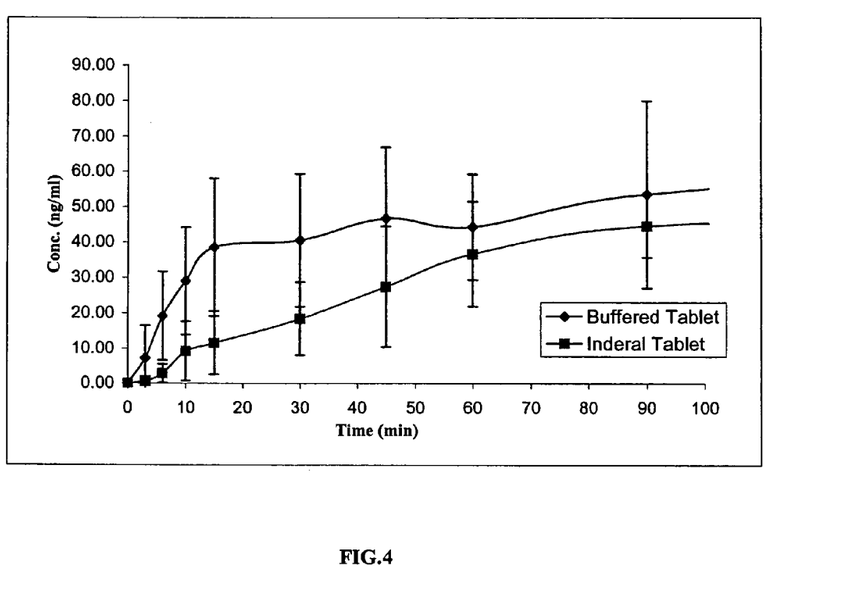
FIG. 4 shows time-plasma concentration profiles (0-100 min) of buffered propranolol tablets of the invention and Inderal (conventional tablets) in 8 male healthy subjects (*$p<0.05$, **$p<0.01$).

Clinical Pharmacokinetic Study of Buffered Propranolol Sublingual Tablets Compared to Conventional Propranolol Tablets I. Methodology of Study The study was conducted using a single dose, two-treatment, cross-over design. Eight healthy male subjects were randomly assigned to two groups, one with 4 of the subjects receiving a single dose of buffered tablets sublingually, and the other with the rest of the subjects receiving a single dose of conventional tablets (Inderal) sublingually. The doses of propranolol in the buffered tablets and conventional tablets employed in the trail are identical at 40 mg. After 15 minutes sublingually, each subject swallowed the dissolved propranolol and followed by swallowing additional 1 cup of water. After a washout period of 2 weeks, each subject was crossed over to receive the other formulation. Venous blood samples (5 ml) were collected via a cannula inserted in the antecubital vein at 0, 3, 6, 10, 15, 30, 45, 60, 90, 150, 300, and 420 minutes after drug administration. Drug concentrations in plasma were determined by HPLC. Propranolol plasma concentration versus time profiles was then analyzed using a non-compartmental model. The time-plasma concentration profiles of the two formulations were plotted as shown in FIG. 3 and FIG. 4.

II. Results

Pharmacokinetic parameters of buffered propranolol tablet and Inderal (conventional tablet) after sublingual administration in eight male healthy subjects (By Paired-Samples T-test) in the above study were calculated using non-compartment model and summarized in Table 3.

TABLE 3

| Parameters | Buffered Tablets (Mean ± SD) | Inderal Tablets (Mean ± SD) | p-Values |
|---|---|---|---|
| $T_{eff}$ (min) | 8.5 ± 7.7 | 38.8 ± 20.4 | 0.004 |
| $T_{max}$ (min) | 78.8 ± 50.6 | 99.4 ± 44.6 | 0.173 |
| $C_{max}$ (ng/ml) | 58.3 ± 21.3 | 51.7 ± 11.8 | 0.287 |
| $\lambda z$ (min$^{-1}$) | 0.0036 ± 0.0011 | 0.0036 ± 0.0010 | 0.826 |
| $t_{1/2}$ (min) | 203 ± 48 | 210 ± 68 | 0.074 |
| $AUC_{0-15\ min}$ (ng · min/ml) | 310.6 ± 177.8 | 79.3 ± 68.8 | 0.019 |
| $AUC_{0-30\ min}$ (ng · min/ml) | 908.8 ± 450.4 | 306.9 ± 209.0 | 0.015 |
| $AUC_{0-420\ min}$ (ng · min/ml) | 16582 ± 6634 | 13305 ± 4683 | 0.067 |
| $AUC_\infty$ (ng · min/ml) | 22973 ± 10096 | 19864 ± 10142 | 0.269 |
| $V_z/F$ (L) | 608.3 ± 287.5 | 694.4 ± 242.1 | 0.275 |
| CL/F (ml/min) | 2312.7 ± 1765.8 | 2569.8 ± 1399 | 0.622 |
| $MRT_{0-420\ min}$ (min) | 179.6 ± 18.0 | 187.3 ± 24.4 | 0.173 |

In Table 3, the abbreviations have the following meanings:
$T_{eff}$—Time to reach the minimum effective plasma concentration (20 ng/ml);
$T_{max}$—Time of occurrence for the maximum (peak) drug concentration;
$C_{max}$—Maximum concentration of the drugs;
$\lambda z$—First order rate constant associated with the terminal (log-linear) portion of the curve;
$t_{1/2}$—Half-life of the drugs;
AUC—Area under a curve;
$V_z/F$—Volume of distribution based on the terminal phase;
CL/F—Total body clearance; and
MRT—Mean residence time.

III. Conclusion

Our buffered propranolol tablets resulted in a significantly higher and faster onset of plasma concentration than the conventional tablet when administered in the same manner. There was no significance difference in the total systemic exposure ($AUC_\infty$)

Many modifications and variations of the embodiments described herein may be made without departing from the scope, as is apparent to those skilled in the art. The specific embodiments described herein are offered by way of example only.

What is claimed is:

1. A method for enhancing absorption of a medicament comprising propranolol or a pharmaceutically acceptable form thereof across a mucosal membrane, comprising administering said medicament in combination with a suitable buffering agent in an amount that provides a pH of about 7.6 at said membrane.

2. The method of claim 1, wherein the medicament is administered sublingually.

3. The method of claim 2, wherein the pharmaceutically acceptable form is an acidic salt.

4. The method of claim 3, wherein the salt is hydrochloride.

5. The method of claim 1, wherein the buffering agent is a phosphate buffer.

6. The method of claim 5, wherein the buffering agent is disodium hydrogen phosphate, sodium dihydrogen phosphate or a combination thereof.

7. A medicament suitable for sublingual administration to a subject, comprising an effective amount of propranolol or a pharmaceutically acceptable form thereof, and a pharmaceutically acceptable carrier, wherein the medicament is buffered with a suitable buffering agent in an amount that provides a pH of about 7.6 at a sublingual area of said subject.

8. The medicament of claim 7, wherein the pharmaceutically acceptable form is a salt.

9. The medicament of claim 8, wherein the salt is hydrochloride.

10. The medicament of claim 7, wherein the buffering agent is a phosphate buffer.

11. The medicament of claim 10, wherein the buffering agent is disodium hydrogen phosphate, sodium dihydrogen phosphate or a combination thereof.

12. The medicament of claim 7, wherein the medicament is formulated as a tablet.

13. The medicament of claim 12, wherein the tablet contains from about 20 mg to about 80 mg of propranolol.

14. A method for treating or ameliorating a disease selected from the group consisting of essential and renal hypertension, angina pectoris, anxiety tachycardia, essential tremor, atrial fibrillation, and hypertrophic obstructive cardiomyopathy, in a subject comprising administering a therapeutically effective amount of propranolol across a mucosal membrane of the subject, wherein said propranolol is buffered with a suitable buffering agent in an amount that provides a pH of about 7.6 at said membrane.

* * * * *